United States Patent [19]

Eisner et al.

[11] Patent Number: 5,185,365
[45] Date of Patent: Feb. 9, 1993

[54] INSECT DETERRENT AZAMCROLIDES

[75] Inventors: Thomas Eisner; Athula B. Attygalle; Kevin D. McCormick, all of Ithaca, N.Y.

[73] Assignee: Cornell Research Foundation, Inc., Ithaca, N.Y.

[21] Appl. No.: 903,347

[22] Filed: Jun. 24, 1992

[51] Int. Cl.$^5$ .................. A01N 43/22; C07D 267/00
[52] U.S. Cl. .................... 514/450; 540/457
[58] Field of Search .................... 540/457; 514/450

[56] References Cited

U.S. PATENT DOCUMENTS

| | | | |
|---|---|---|---|
| 3,704,246 | 11/1972 | Bodanszky | 540/552 |
| 4,849,447 | 7/1989 | Jacobs | 514/450 |
| 4,886,792 | 12/1989 | Djokic et al. | 514/183 |
| 5,089,521 | 2/1992 | Wink et al. | 514/450 |

Primary Examiner—Marianne M. Cintins
Assistant Examiner—John Peabody

[57] ABSTRACT

The insect deterrent azamacrolide

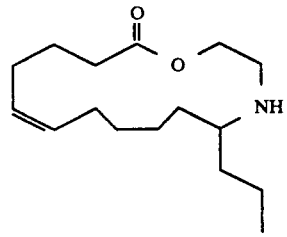
(I)

and other insect deterrent azamacrolides have been recovered from droplets formed at the ends of pupal hairs of the Mexican bean beetle *Epilachna varivestis* or synthesized from (I).

12 Claims, No Drawings

INSECT DETERRENT AZAMCROLIDES

This invention was made at least in part with Government support under Grants AI-02908 and AI-12020 from National Institutes of Health.

TECHNICAL FIELD

The invention relates to isolated and novel azamacrolides for use for protecting against harmful pests, compositions containing them, and their use for insect deterrent purposes.

BACKGROUND OF THE INVENTION

For many years now, several powerful and effective insecticides have been used to protect food and fiber crops. More recently, there has been a great deal of controversy about the effect of these on the environment and some of the insecticides which have been in common use have been banned. Furthermore, other insecticides which are still in use are considered to be potentially harmful to the environment but are required to be used for lack of other alternatives.

As a result, a search has been going on for "biorational pesticides". These are compositions which would deter insects or other pests but would have no or minimal harmful effect on the environment.

SUMMARY OF THE INVENTION

It has been discovered herein that azamacrolides recovered from oily droplets formed on the pupal hairs of the Mexican bean bettle, *Epilachna varivestis*, and hydrogenated derivative thereof, are excellent insect deterrents.

The compounds of the invention herein are substantially pure azamacrolides having the structural formula

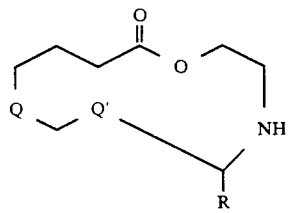

wherein Q is CH=CH or $CH_2$, $(CH_2)_2$, wherein Q' is $CH_2$, $(CH_2)_3$, $(CH_2)_4$ or CH=CH—$CH_2$ and R is ethyl or propyl.

The invention herein in another embodiment is directed to an insect deterrent composition comprising an emulsion in water of an insect deterrent effective amount of one or more azamacrolides having the structural formula

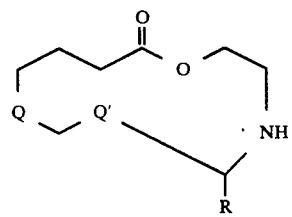

wherein Q is CH=CH or $CH_2$, $(CH_2)_2$, wherein Q' is $CH_2$, $(CH_2)_3$, $(CH_2)_4$ or CH=CH—$CH_2$ and R is ethyl or propyl.

The invention herein in still another embodiment is directed at a method of deterring insects at a locus which comprises treating the locus with an insect deterrent effective amount of one or more azamacrolides having the structural formula

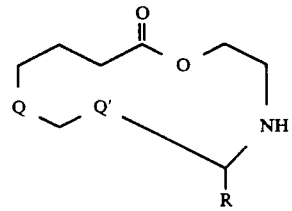

wherein Q is CH=CH or $CH_2$, $(CH_2)_2$, wherein Q' is $CH_2$, $(CH_2)_3$, $(CH_2)_4$ or CH=CH—$CH_2$ and R is ethyl or propyl.

The term "substantially pure" is used herein to mean 99.9+% pure.

DETAILED DESCRIPTION

The substantially pure azamacrolides which are recovered from oily droplets formed on the pupal hairs of the Mexican bean beetle include those having the following structural formulas:

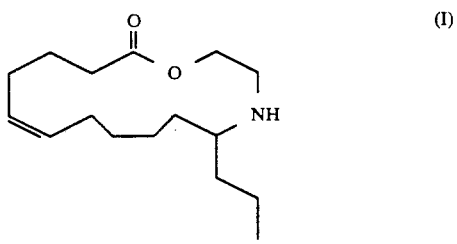
(I)

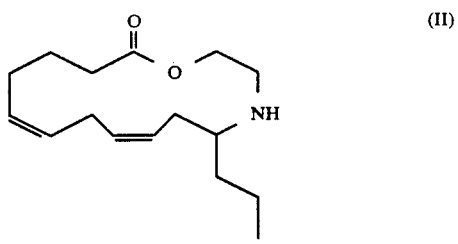
(II)

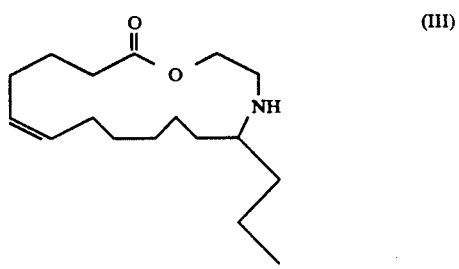
(III)

-continued

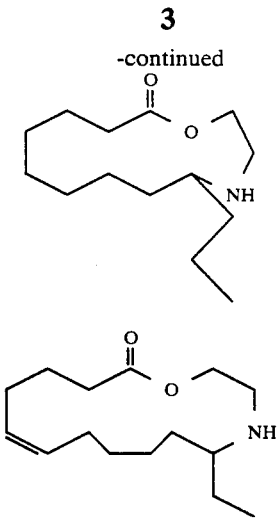

In addition the following substantially pure azamacrolide has been prepared by hydrogenation of compound (I).

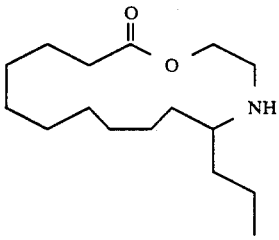

Compound (I) has the IUPAC name (5Z)-11-propyl-12-azacyclotetradec-5-en-14-olide. It has been named "epilachnene" by the inventors herein. It is the major product isolated from the volatazable material from the droplets obtained from the pupal hair of the Mexican bean beetle and makes up about 90% of said volatizable material.

Compound (II) has the IUPAC name (5Z,8Z)-11-propyl-12-azacyclotetradec-5,8-dien-14-olide. It has been named "epilachnadiene" by the inventors herein. It has been found to make up about 5% of the volatizable material from the droplets from Mexican bean beetle pupal hair.

Compound (III) has the IUPAC name (5Z)-12-propyl-13-azacyclopentadec-5-en-15-olide. It has been named "homoepilachnene" by the inventors herein. It has been found to make up about 1% of the volatizable material from the droplets from Mexican bean beetle pupal hair.

Compound (IV) has the IUPAC name 9-propyl-10-azacyclododecan-12-olide. It has been found to make up about 1% of the volatizable material from the droplets form Mexican bean beetle pupal hair.

Compound (V) has the IUPAC name (5Z)-11-ethyl-azacyclotetradec-5-en-14-olide. It has been found to make up about 1% of the volatizable material from the droplets from Mexican bean beetle hair.

Compound (VI) has the IUPAC name 11-propyl-12-azacylotetradecan-14-olide. It has been named "epilachnane" by the inventors herein.

The compounds (I), (II), (III), (IV), (V) and (VI) are recovered herein as liquids.

The compounds (I), (II), (III), (IV) and (V) are each readily recovered in substantially pure form by gas chromatographic separation of the Mexican bean beetle pupal hair droplets per se or of residue recovered from sulfuric acid extraction of the pupae (having the oily droplets thereon). The gas chromatographic separation is readily carried out using methyl silicone as a stationary phase and programming of the oven temperature to increase from 60° C. to 250° C.

The pupae are obtained for supplying the starting material by having the Mexican bean beetles (commonly found in the United States on bean, i.e., *Phaseolus vulgaris*, leaves) lay eggs on the bean leaves, letting the eggs hatch, having the larvae that emerge feed on the bean leaves until the larvae pupate thereon and recovering the pupae from the bean leaves. The pupae are covered with cuticular hairs, and about a day after pupation, the tiny oily droplets appear at the end of the hairs and remain there.

As indicated above, the compounds (I)-(V) can be isolated from the droplets per se. In this case, the droplets can be readily gathered using a capillary tube and the capillary tube with the droplets drawn thereinto can be used to charge a gas chromatograph for the isolation of pure compounds.

Preferably however, where a large amount of starting material is desired, the starting material is readily recovered by admixing pupae (with droplets thereon) with dilute (e.g., 0.5% to 3%) sulfuric acid, crushing the pupae in the admixture, filtering to remove the solid residue, admixing the filtrate with methanol and maintaining the admixture, diluting with an equal volume of water, extracting with ether, recovering the aqueous phase, making the aqueous phase alkaline, extracting with chloroform, drying the chloroform phase over sodium sulfate and then evaporating to leave a residue that is similar in constitution to the original droplets.

The compound (VI) is readily obtained by hydrogenating compound (I) using 10% Pd on C as hydrogenation catalyst.

The azamacrolide compounds described above are readily formulated into insect deterrent compositions.

A preferred composition is the aqueous emulsion described earlier and the preferred azamacrolide for inclusion therein is that having formula (I). The percentage of the composition which is emulsifing agent normally depends on the emulsifing agent which is used. Typically, the emulsifying agent is used in an amount ranging from about 0.2% to about 30% of the composition and often is used at a level of from about 15% to about 25%. The emulsion can be made up as a concentrate and diluted with water for application. In the emulsion for application, the concentration of the azamacrolide ordinarily ranges from 1 ppm to 10,000 ppm. Preferred emulsifying agents are those normally utilized in foods and include sorbitan esters, ethoxylated and propoxylated mono- or diglycerides, acetylated mono- or diglycerides, lactylated mono- or diglycerides, citric acid esters of mono- or diglycerides, sugar esters, polysorbates and polyglycerol esters. Preferred emulsifier is polyoxyethylene sorbitan monolaurate which is sold under the name Tween 20 ®.

The azamacrolide compounds described above are also formulated in effective concentrations, e.g., 1 ppm to 10,000 ppm, in combination with other liquid carriers, e.g., alcohols, e.g., isopropanol and glycols; ketones, e.g., acetone, methyl ethyl ketone, methyl isobutyl ketone and cyclohexanone; ethers; aromatic or aralkyl hydrocarbons, e.g., benzene, toluene and xylene; petroleum fractions, e.g., kerosene, and light mineral oils; and chlorinated hydrocarbons, e.g., carbon tetrachloride, perchloroethylene and terchloroethane. Mixtures of different liquids are often suitable.

The azamacrolide compounds described above are also formulated in effective concentrations, e.g., 1 ppm to 10,000 ppm in combination with solid carriers including, for example, natural and synthetic clays and silicates (e.g., natural silicas such as diatomaceous earths, magnesium silicates such as talcs, magnesium aluminum silicates such as kaolinites, montmorillonites and micas), calcium carbonate, calcium sulfate, ammonium sulfate, elements such as carbon and sulfur, natural and synthetic resins such as coumarone resins, polyvinyl chloride and styrene polymers and copolymers, bitumen, waxes, and solid fertilizers such as superphosphates.

Just as ants and other insects are deterred on contact with Mexican bean beetle pupae, insects are deterred on contact with the compounds and compositions of the instant invention.

The compounds and compositions of the instant invention have biomedical and/or agrochemical application.

They have anti-feedant activity (deters insects from feeding on plants) against several pests including ants, Japanese beetles, fall armyworms, locusts, grasshoppers, tobacco hornworms, tobacco budworms, caterpillars, gypsy moths, rice weevils, aphids, cotton ball moths and many others.

For antifeedant utility, the embodiment of this invention applies wherein a locus is treated with a deterrent effective amount of one or more azamacrolides as specified and the locus comprises plants subject to or subjected to attack, seeds of such plants, or the medium in which the plants are growing or are to be grown. The preferred azamacrolide for this purpose is that have the formula (I).

The invention is illustrated by the following example.

EXAMPLE

Mexican bean beetles were obtained from the Boyce Thompson Institute at Cornell University.

The beetles were placed on bean (*Phaseolus vulgaris*) leaves for laying of eggs. In about a week the eggs hatched and larvae emerged on the bean leaves and fed on them. After 3 to 4 weeks, the larvae pupated and the pupae remained attached to the leaves. The pupae are covered with cuticular hairs, and about a day after pupation, tiny droplets of liquid appear at the end of the pupal hairs and remain there.

The pupae were harvested after the appearance of the liquid droplets, and the liquid droplets were recovered by two methods.

In one method, capillary tubes were used to draw the droplets therein.

The second method involved sulfuric acid extraction. In this method, about 500 pupae were deposited in 400 ml of 1% sulfuric acid. A glass rod was used to crush the pupae and the resulting admixture was maintained at room temperature for about two hours. Then filtering was carried out and the filtrate was recovered. The filtrate was admixed with 200 ml of methanol and the resulting admixture was maintained at room temperature for two hours. Then 200 ml more of methanol was admixed, and the resulting admixture was maintained at room temperature for two hours. The resulting admixture was diluted with an equal volume of water and the diluted admixture was extracted three times, each time with 250 ml of ether, and each time the ether phase was discarded. The aqueous phase was made alkaline with 2M NaOH and the alkaline admixture was extracted three times, each time with 200 ml of chloroform. Each time the chloroform phase was recovered and the chloroform phases were combined. The combined chloroform phases were dried over sodium sulfate and then were evaporated to leave a residue of the azamacrolides in the same relative amounts as occur in the initial drops.

In one case the capillary tube filled with droplets was used to charge a gas chromatograph and in a second case the residue from the sulfuric acid extraction was used to charge a gas chromatograph, and in each case gas chromatography was used to isolate the active constituents in substantially pure form. In the gas chromatography, methyl silicone was used as the stationery phase and temperature was programmed to increase from 60° C. to 250° C. The volatilized material was trapped as it emerged, in glass tubes cooled in an ice bath or with dry ice. The gas chromatograph column was equipped with a splitter so that 10% of the volatiles were continuously routed to a detector which indicated when volatiles were emerging.

In both the cases of the capillary recovered droplets and the sulfuric acid extraction recovered residue, the chromatography separation results were the same.

Substantially pure products of structures (I), (II), (III), (IV) and (V) were recovered. The major product had the formula (I) and amounted to about 90% by weight of the volatiles and was essentially 100% pure in contrast to the starting material which contained a substantial proportion of non-volatiles as well as other azamacrolides. Substantially pure product of formula (II) amounted to about 5% by weight of the volatiles and substantially pure products of formulas (III), (IV) and (V) each amounted to about 1% by weight of the volatiles. Analysis of the products was carried out by mass spectrometry and nuclear magnetic resonance spectrometry and was confirmed by microchemical transformation.

A portion of the product of formula (I) was converted to product of formula VI. This was carried out by dissolving the starting material (I) in 100 volumes of ether, adding 10% Pd on C catalyst amounting to 5% by weight of the starting material (I) and stirring under hydrogen at room temperature for 2 hours. The resulting admixture was filtered to remove the catalyst and the ether was evaporated to provide the product of formula (VI).

The products of formulas (I), (II), (III), (IV), (V) and (VI) are readily formulated into aqueous emulsions using 2% by weight polyoxyethylene sorbitan monolaurate and the emulsions are sprayed on cotton plants to deter insects from attacking them.

Many variations of inventive embodiments will be obvious to those skilled in the art. Thus, the inventive embodiments are defined by the claims.

What is claimed is:

1. Substantially pure azamacrolide having the structural formula

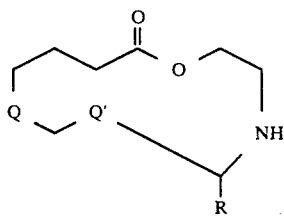

wherein Q is CH=CH or CH₂, (CH₂)₂, wherein Q' is CH₂, (CH₂)₃, (CH₂)₄ or CH=CH—CH₂ and R is ethyl or propyl.

2. The substantially pure azamacrolide of claim 1 which has the structural formula

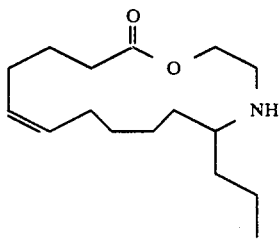

3. The substantially pure azamacrolide of claim 1 which has the structural formula

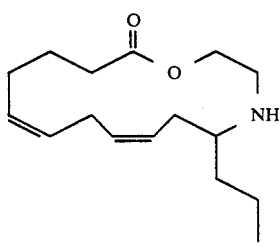

4. The substantially pure azamacrolide of claim 1 which has the structural formula

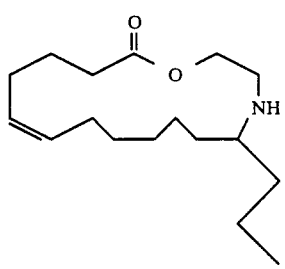

5. The substantially pure azamacrolide of claim 1 which has the structural formula

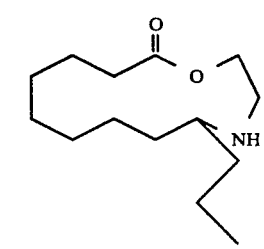

6. The substantially pure azamacrolide of claim 1 which has the structural formula

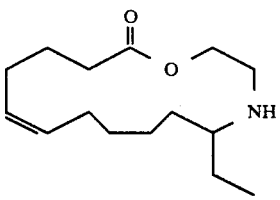

7. The substantially pure azamacrolide of claim 1 which has the structural formula

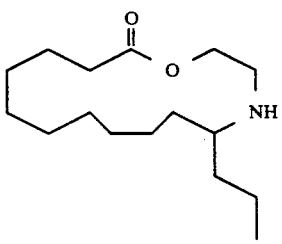

8. An insect deterrent composition comprising an emulsion in water of an insect deterrent effective amount of one or more azamacrolides having the structural formula

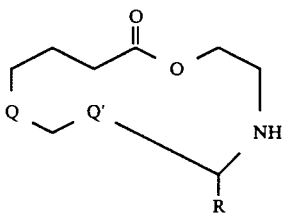

wherein Q is CH=CH or CH₂, wherein Q' is CH₂, (CH₂)₃, (CH₂)₄ or CH=CH—CH₂ and R is ethyl or propyl.

9. The insect deterrent composition of claim 8 wherein the azamacrolide consists of that having the structural formula

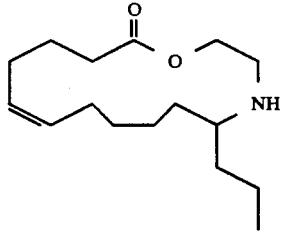

10. A method of deterring insects at a locus which comprises treating the locus with an insect deterrent effective amount of one or more azamacrolides having the structural formula

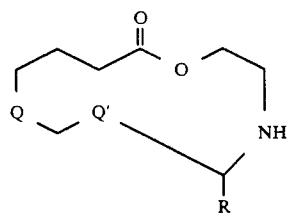

wherein Q is CH=CH or CH₂, wherein Q' is CH₂, (CH₂)₃, (CH₂)₄ or CH=CH—CH₂ and R is ethyl or propyl.

11. A method as claimed in claim 10, wherein the locus comprises plants subject to or subjected to insect attack, seeds of such plants, or the medium in which the plants are growing or are to be grown.

12. The method of claim 11 wherein the azamacrolide consists of that having the structural formula

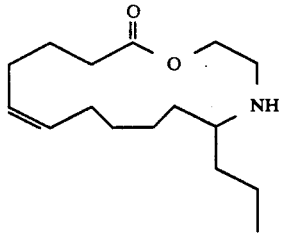

* * * * *

UNITED STATES PATENT AND TRADEMARK OFFICE
CERTIFICATE OF CORRECTION

PATENT NO. : 5,185,365

DATED : February 9, 1993

INVENTOR(S) : Thomas Eisner et al

It is certified that error appears in the above-identified patent and that said Letters Patent is hereby corrected as shown below:

Column 1, lines 50 and 51, after "$CH_2$," in line 50, delete "$(CH_2)_2$," and in line 51, after "$CH_2$," insert -- $(CH_2)_2$, --.

Column 2, lines 1 and 2, after "$CH_2$," in line 1, delete "$(CH_2)_2$," and in line 2, after "$CH_2$," insert --$(CH_2)_2$,--.

Column 2, lines 23 and 24, after "$CH_2$," in line 23, delete "$(CH_2)_2$," and in line 24, after "$CH_2$," insert --$(CH_2)_2$,--.

Claim 1 (column 7, lines 11 and 12) in line 11 after "$CH_2$," delete "$(CH_2)_2$," and in line 12, after "$CH_2$," insert --$(CH_2)_2$,--.

Signed and Sealed this

Seventh Day of December, 1993

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,185,365

DATED : February 9, 1993

INVENTOR(S) : Thomas Eisner et al

It is certified that error appears in the above-identified patent and that said Letters Patent is hereby corrected as shown below:

On title page, item [54], in the title, "AZAMCROLIDES" should be
-- AZAMACROLIDES --.

Column 1, in the title, "AZAMCROLIDES" should be
-- AZAMACROLIDES --.

Signed and Sealed this

First Day of March, 1994

Attest:

BRUCE LEHMAN

*Attesting Officer*    *Commissioner of Patents and Trademarks*